(12) United States Patent
Davies et al.

(10) Patent No.: US 6,455,270 B1
(45) Date of Patent: *Sep. 24, 2002

(54) METHOD FOR INHIBITING EUKARYOTIC PROTEIN KINASES

(75) Inventors: Julian E. Davies, Vancouver; Barbara Waters, Delta; Geeta Saxena, Vancouver, all of (CA)

(73) Assignee: TerraGen Discovery Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/688,545

(22) Filed: Oct. 16, 2000

Related U.S. Application Data

(63) Continuation of application No. 09/174,261, filed on Oct. 16, 1998, now Pat. No. 6,132,984.
(60) Provisional application No. 60/062,516, filed on Oct. 17, 1997.

(51) Int. Cl.[7] .............................. C12Q 1/37; C12Q 1/00
(52) U.S. Cl. .............................. 435/23; 435/4; 435/886
(58) Field of Search ........................... 435/23, 4, 886

(56) References Cited

U.S. PATENT DOCUMENTS

| | | | |
|---|---|---|---|
| 4,536,474 A | 8/1985 | Yamamoto et al. | 435/23 |
| 4,937,195 A | 6/1990 | Yamamoto et al. | 435/23 |
| 5,143,839 A | 9/1992 | Blumberg et al. | 435/23 |
| 5,451,518 A | 9/1995 | Kolesnick | 435/23 |
| 5,770,392 A | 6/1998 | Davies et al. | 435/23 |
| 6,132,984 A | * 10/2000 | Davies et al. | 435/23 |

OTHER PUBLICATIONS

Levitzki, A. and A. Gazit, "Tyrosine Kinase Inhibition: An Approach to Drug Development", Science 267:1782–1788, Mar. 24, 1995.

Waters, B. et al., "Protein tyrosine phosphorylation in streptomycetes", FEMS Microbiology Letters 120: 187–190, 1994.

Natsume et al., "Calcium Signal Modulators Inhibit Aerila Mycelium Formation in *Streptomyces alboniger*", J. Antibiotics 45: 1026–1028, 1992.

(List continued on next page.)

*Primary Examiner*—Louise N. Leary
(74) *Attorney, Agent, or Firm*—Fish & Neave; James F. Haley, Jr.; Karen E. Brown

(57) ABSTRACT

Lichen-derived organic acids such as vulpinic acid and usnic acid have been found to be effective inhibitors of eukaryotic protein kinase activity. Thus, eukaryotic protein kinase activity present in a sample or organism can be inhibited by adding to the sample or organism an effective inhibitory amount of a lichen-derived organic acid.

5 Claims, 1 Drawing Sheet

VULPINIC ACID $C_{19}H_{14}O_5$ (322)

OTHER PUBLICATIONS

Altschul, S.F., Gish, W., Miller, W., Myers, E. and Lipman, D. 1990, "Basic local alignment tool", J. Mol. Biol. 215:403–410.

Av–Gay, Y. and Davies, J. 1997, "Components of eukaryotic–like protein signaling pathways in *Mycobacterium tuberculosis* ", Microbial & Comparative Genomics 2:63–73.

Georgiou, G., Lin, S–C., and Sharma, M., 1992, Surface–active compounds from microorganisms, Biotechnology, 10: 60–65.

Gerrard, J., Lloyd, R., Barsby, T., Haden, P., Kelly, M and Anderson, R., 1997, Massetolides A–H, antimycobacterial cyclic depsipeptides produced by two Pseudomonads isolated from marine habitats. J. Nat. Prod., 60:223–229.

Huncck, S. and Yoshimura, I., 1996 "Identification of lichen substances", Springer–Verlag, Berlin.

Lane, D., 1991, 16S/23S rRNA sequencing, p. 115–175 In Stackebrandt, E. and Goodfellow, M., (ed.), "Nucleic acid techniques in bacterial systematics", John Wiley and Sons, Chichester.

Lauterwein, M., Oethinger, M., Belsner, K., Peters, T. and Maree, R. 1995, "In vitro activities of the lichen secondary metabolites vulpinic acid, (+)–usnic acid and (–) –usnic acid against acrobic and anacrobic microorganisms", Antimicrobial Agents and Chemotherapy, 39: 2541–2543.

Stachelhaus, T., Schneider, A. and Marahiel, M., 1996, "Engineered biosynthesis of peptide antbiotics", Biochemical Pharmacology, 52: 177–186.

Toraya, T., Maoka, T., Tsuji, H. and Kobayashi, M., 1995, "Purification and structural determination of an inhibitor of starfish oocyte maturation from a Bacillus species", Applied and Environmental Micro, 5: 1799–1804.

Hong et al., "Effects of protein kinase inhibitors on in vitroprotein phosphorylation and cellular differentiation of *Streptomyces griseus*", Mol. Gen. Genetics 236: 347–354, 1993.

Kennelly et al., "Fancy Meeting You Here!, A Fresh Look at 'Prokaryotic' Protein Phosphorylation", J. Bacteriol, 178: 4759–4764, 1996.

Karin et al., "Transcriptional control by protein phosphorylation: signal transmission from cell surface to nucleus", Current Biology 5: 747–757, 1995.

Ray, L.B., "Signals and Communication," Science 268: 183, 1995.

Casey, P.J., "Protein Lipidation in Cell Signaling", Science 268: 224–225, 1995.

Burbulys et al., "Initiation of Sporulation in *B. subtilis* Is controlled by a Multicomponent Phosphrelay" Cell 64: 545–552.

Stock et al., "Protein Phosphorylation and Regulation of Adaptive Responses in Bacteria", Micriobiol. Reviews 53: 450–490, 1989.

South et al., "Tyrosine Kinase activity in *Pseudomonas aeruginosa*", Molecular Microbiol. 12: 903–910, 1994.

Chow et al., "Protein tyrosine phosphorylation in *Mycobacterijm tuberculosis*", FEMS Microbiol. Lett. 124: 203–208, 1990.

Li et al., "Cloning, Purification and Properties of a Phosphotyrosine Protein Phosphatase from *Streptomyces coelicolor* A3(2)", J. Bacteriol. 178: 136–142, 1996.

Frasch et al., "Tyrosine Kinase in *Myxococcus xanthus*, a Multicellular Prokaroyte", preprint of article submitted to J. Bacteriol, 1996.

Zhang, C–C., "Bacterial Signalling Involving Eukaryotic––type Protein Kinases" Molecular Microbiol. 20:91–5, 1996.

Zhang et al., "Identification of a Putative Eukaryotic–Like Protein Kinase Family in the Developmental Bacterium *Myxococcus xanthus*" J. Bacteriol. 174: 5450–5453, 1992.

Meydan et al., "Inhibition of acute lymphoblastic leukemia by a Jak–2 inhibitor", Nature 379: 645–648, 1996.

Leukemia–fighting drug found to work in mice, Vancouver Sun, Feb. 15, 1996, p. A11.

Clark et al., "Integrins and Signal Transduction: The Road Taken", Science 268: 233–234, 1995.

Machyl–Rosen, D., "Localization of Protein Kinases by Anchoring Proteins: A Theme in Signal Transduction", Science 268, 1995.

De Franco et al., "Tyrosine Phosphatases and Antibody Response", Science 268: 263–264, 1995.

* cited by examiner

VULPINIC ACID $C_{19}H_{14}O_5$ (322)

*(+/−) USNIC ACID $C_{18}H_{16}O_7$ (344)

METHOD FOR INHIBITING EUKARYOTIC PROTEIN KINASES

This application is a condition of application Ser. No. 09/174,261 filed Oct. 16, 1998 now U.S. Pat. No. 6,132,984 and is a regular application filed under 35 USC § 111(a) claiming priority from U.S. Provisional Application Ser. No. 60/062,516 filed Oct. 17, 1997.

BACKGROUND OF THE INVENTION

This application relates to a method for inhibiting eukaryotic protein kinases using lichen-derived organic acids such as vulpinic acid and usnic acid.

Kinase and phosphatase enzymes play important roles in the regulation of both eukaryotic and prokaryotic cells. For example, in eukaryotic cells, the control of proliferation and differentiation is achieved by multiple signal transduction pathways that are regulated by the coordinated action of protein kinases and phosphatases.

Kinase activity in eukaryotes can be classified as one of three types: those enzymes which phosphorylate tyrosine residues; those which are specific for serine or threonine residues; and those which have dual specificity for both tyrosine and serine/threonine residues. Because of the importance of these enzymes in eukaryotic regulatory processes, it would be highly desirable to be able to inhibit kinases of the various classes selectively to assist in the elucidation of kinase and phosphatase mediated pathways, particularly those that may be of medical significance. In addition, selective kinase or phosphatase inhibitors have potential uses as therapeutics. For example, it has been reported that a tyrosine kinase blocker designated AG-940 specifically inhibits the Jak-2 protein tyrosine kinase which is deregulated and constitutively activated in the leukemic cells of acute lymphoblastic leukemia (ALL) patients. Meydan, et al. "Inhibition of acute lymphoblastic leukaemia by a Jak-2 inhibitor", Nature 379: 645–648 (1996). This inhibition induced changes in cells consistent with entry into apoptosis when tested in vitro. Further, the intravenous administration of the inhibitor into mice previously injected with ALL cells has been shown to be effective to eradicate the ALL cells from the marrow.

Notwithstanding the potential uses of kinase and phosphatase inhibitors, the number of known and characterized inhibitors is quite small. Staurosporine and K-252a are known to act as generalized kinase inhibitors, while herbimycin and radicol specifically inhibit tyrosine kinases, albeit with fairly-low effectiveness. There are no known specific inhibitors for the MAP kinase family, an important group of enzymes thought to be central in the transmission of a wide variety of signals received at the cellular membrane to the transcriptional and replication machinery of the nucleus.

To facilitate the identification of new kinase and phosphatase inhibitors, we have developed an assay which is described in our prior U.S. Pat. No. 5,770,392, issued Jun. 23, 1998 and in a PCT Publication No. WO98/17822 claiming priority therefrom, which are incorporated herein by reference. This assay basically involves the steps of:

adding the material to be tested for kinase inhibitory activity to a growing culture of a prokaryotic organism such as a streptomycete;

allowing the culture to grow for a period of time in the presence of the material; and observing the culture for altered development relative to development of the prokaryotic organism grown in the absence of the material. Observation of altered development is indicative that the material has activity as an inhibitor of post-translational protein phosphorylation. In particular, the material to be tested can be added to a growing culture of the prokaryotic organism by placing a carrier disk bearing the material on a freshly seeded plate. Inhibition of the development of aerial mycelia and spore formation is an indicator that the material has activity as an inhibitor of post-translational protein phosphorylation.

SUMMARY OF THE INVENTION

Using the assay method of our prior invention, we have screened a number of lichen extracts. Surprisingly, the majority of these extracts exhibited the ability to inhibit sporulation of our preferred tester strain Streptomyces 85E, suggesting that there might be a few common inhibitors produced in a wide variety of lichens. Following this line of reasoning, it was discovered that lichen-derived organic acids such as vulpinic acid and usnic acid are effective inhibitors of eukaryotic protein kinase activity. Thus, the present invention provides a method for inhibiting eukaryotic protein kinase activity present in a sample or organism comprising the step of adding to the sample or organism an effective inhibitory amount of a lichen-derived organic acid.

DETAILED DESCRIPTION OF THE INVENTION

Although eukaryotic and prokaryotic protein kinases generally have different substrate specificities, it has been observed[]that in some prokaryotic organisms eukaryote-like kinase and phosphatase activities may complement the two component systems typical of bacteria. In particular, streptomycetes, (Waters et al., "Protein tyrosine phosphorylation in streptomycetes", FEMS Microbiology Letter 120: 187–190 (1994); Li et al, "Cloning purification and properties of a phosphotyrosine protein phosphatase from Streptomyces coelicolor A3(2)", J. Bact. 178: 136–142 (1996)); Myxococcus xanthus (Zhang et al., "Identification of a putative eukaryotic-like protein kinase family in the developmental bacterium Myxococcus xanthlus", J. Bact. 174: 5450–5453 9192); and cyanobacterial species. (Zhang, C-C, "Bacterial signaling involving eukaryotic-type protein kinases", Molec. Microbiol. 20: 9–15 (1996)). Because of this, certain microbes to can be used to provide an assay for screening materials for activity as inhibitors of eukaryotic post-translational protein phosphorylation, and in particular for protein kinase activity.

We have used a wild strain of Streptomyces isolated from soil and designated Streptomyces WEC478-85E (hereinafter strain 85E) to test lichen extracts. Strain 85E has been deposited with the American Type, Culture Collection in accordance with the provisions of the Budapest treaty and has been assigned Accession Number ATCC 55824.

In the test assay, the lichen-extract to be tested was applied to a filter paper disk and then placed on a plate which has been freshly seeded with the strain 85E test organism. The test organism is then allowed to grow in the presence of the filter paper disk for a period of 24 to 36 hours, after which the organism is evaluated for altered development in the zone around the disk. An observation of an inhibition of the formation of aerial mycelia and spores, without inhibition of the growth of vegetative mycelia is particularly indicative of the presence of an inhibitor of post-translational phosphorylation.

Figure 1:
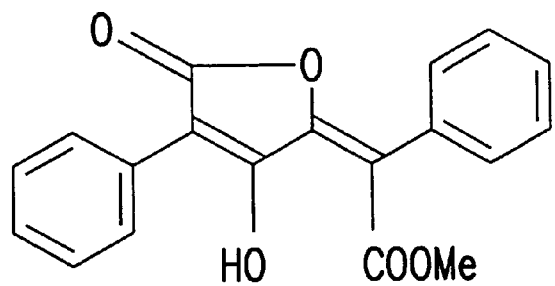
FIG. 1 shows the structure of vulpinic acid.
Figure 2:
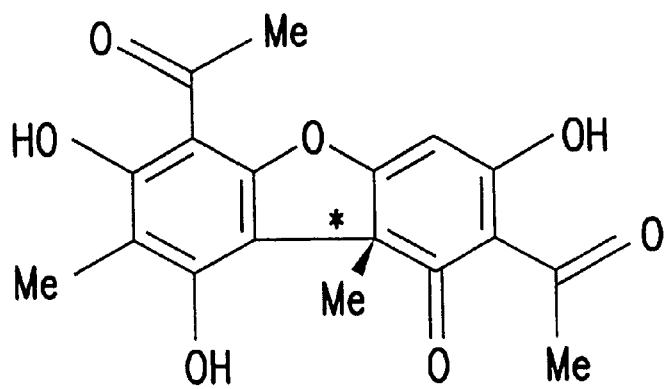
FIG. 2 shows the structure of usnic acid.

Extracts from 62 species of lichens were screened, of which 52 extracts were found to inhibit sporulation of tester strain Streptonzyces 85E. Because of the breadth of inhibitory results found, two widely distributed lichen compounds, vulpinic acid (FIG. 1) and usnic acid (FIG. 2) were obtained in purified form and tested for activity as inhibitors of sporulation in the first instance and then as kinase inhibitors.

Usnic acid is a widely distributed lichen compound. Huneck and Yoshimura, *Identification of Lichen Substances*, Springer-Verlag, Berlin (1996) list 16 lichen genera from which this compound has been isolated. Vulpinic acid is usually isolated from Letharia vulpina, but is also found in other lichen species. Both of these compounds have been reported to have antibacterial activities (Lauterwein et al., *Antimicrobial Agents and Chemotherapy* 39: 2541–2543 (1995)) but neither has previously been identified as a kinase inhibitor. Both of the purified compounds were found to inhibit sporulation in Streptomyces 85E. Both compounds were also found to inhibit human c-Src kinase. Minimal inhibition of Protein Kinase C was also observed for both compounds. Although the kinase inhibitory activity was not particularly potent with respect to the two enzymes tested, the sporulation inhibition activity is very marked and it is possible that other eukaryotic kinases may be more strongly affected by these compounds.

The present invention provides recognition of a new class of compounds, namely lichen-derived organic acids, which may be used as inhibitors of eukaryotic protein kinase for investigational and therapeutic purposes. While the invention is exemplified through two specific lichen-derived organic acids, namely vulpinic acid and usnic acids, other lichen-derived organic acids which inhibit sporulation of Streptomyces 85E might also be employed.

The invention will now be further described and illustrated by way of the following, non-limiting examples.

EXAMPLE 1

Extracts (in methanol:acetone, 1:1) were prepared from 62 species of lichens and 52 extracts were found to inhibit sporulation of the tester strain Streptomyces 85E. Prior to initiation of attempts to purify active compounds from many different lichen species, two widely distributed lichen compounds were tested: namely vulpinic acid and usnic acid (both obtained from Sigma).

Inhibition of Sporulation in Streptomyces 85E

| Compound applied to disc | Inhibition zone |
| --- | --- |
| 10 ug usnic acid | 15 mm |
| 10 ug vulpinic acid | 15 mm |

Growth of the vegetative mycelia was not inhibited. The inhibition of sporulation was persistent, lasting for at least 2 to 3 days. The presence of usnic acid and vulpinic acid in several of the positive lichen extracts was confirmed by co-TLC with the authenticated compounds followed by an agar overlay test with Streptomyces 85E. Sporulation was inhibited in zones over the spots of these compounds and also over spots with the same $_RF$ value in the lichen extracts. At least 16 of the extracts were found to contain usnic acid and at least 5 contain vulpinic acid.

Examples of Inhibition of Protein Kinase Activities:

I. Human c-Src kinase incubated 30 min. at 30° C. with 5 ug usnic acid or-vulpinic acid:

| Control reaction 0.2 unit c-Src | 0.2 unit c-Src + usnic acid | 0.2 unit c-Src + vulpinic acid |
| --- | --- | --- |
| 0.562 | 0.417 | 0.483 |

II. Human c-Src incubated 5 min. at 30° C. with 5 ug usnic acid or 5 ug vulpinic acid:

| Control reaction 0.2 unit c-Src | 0.2 unit c-Src + usnic acid | 0.2 unit c-Src + vulpinic acid |
| --- | --- | --- |
| 0.208 | 0.120 | 0.180 |

III. Protein Kinase C incubated 30 min. at 30° C. with 5 ug usnic acid or 5 ug vulpinic acid:

| Control reaction 10 ng PKC | 10 ng PKC + usnic acid | 10 ng PKC + vulpinic acid |
| --- | --- | --- |
| 0.289 | 0.234 | 0.230 |

5 ug in the 50 ul PTK reaction mixture represents a concentration of about 300 uM for both of these compounds and twice that in the 25 ul PKC reactions. Thus, inhibition was detected for this particular protein tyrosine kinase and only minimally inhibitory for protein kinase C. Other protein kinases may show greater or lesser levels of inhibition.

What is claimed is:

1. A method for inhibiting eukaryotic protein kinase activity present in a sample or organism comprising the step of adding to the sample or organism an effective inhibitory amount of a lichen derived organic compound which inhibits the sporulation of Streptomyces.

2. The method of claim 1 wherein the eukaryotic protein kinase is a Protein Kinase C.

3. The method of claim 1 wherein the eukaryotic protein kinase is a human protein kinase.

4. The method of claim 3 wherein the human protein kinase is a c-Src protein kinase.

5. A method for inhibiting eukaryotic protein kinase activity present in a sample or organism comprising the step of adding to the sample or organism an effective inhibitory amount of a lichen extract which inhibits the sporulation of Streptomyces.

* * * * *